(12) United States Patent
Van Loosdrecht et al.

(10) Patent No.: US 9,963,829 B2
(45) Date of Patent: May 8, 2018

(54) EXTRACELLULAR POLYMERS FROM GRANULAR SLUDGE AS SIZING AGENTS

(71) Applicant: Technische Universiteit Delft, Delft (NL)

(72) Inventors: Marinus Cornelis Maria Van Loosdrecht, Delft (NL); Lin Yuemei, Delft (NL); Tommaso Lotti, Delft (NL)

(73) Assignee: TECHNISCHE UNIVERSITEIT DELFT, Delft (NL)

( * ) Notice: Subject to any disclaimer, the term of this patent is extended or adjusted under 35 U.S.C. 154(b) by 6 days.

(21) Appl. No.: 15/099,191

(22) Filed: Apr. 14, 2016

(65) Prior Publication Data
US 2016/0230345 A1    Aug. 11, 2016

Related U.S. Application Data

(63) Continuation of application No. PCT/NL2014/050718, filed on Oct. 14, 2014.

(30) Foreign Application Priority Data

Oct. 14, 2013   (NL) ...................................... 2011609

(51) Int. Cl.
| | | |
|---|---|---|
| *D21H 17/21* | (2006.01) | |
| *D21H 21/16* | (2006.01) | |
| *D21H 17/22* | (2006.01) | |
| *C12P 19/04* | (2006.01) | |
| *D21H 17/24* | (2006.01) | |

(52) U.S. Cl.
CPC .............. *D21H 21/16* (2013.01); *C12P 19/04* (2013.01); *D21H 17/21* (2013.01); *D21H 17/22* (2013.01); *D21H 17/24* (2013.01)

(58) Field of Classification Search
CPC ........ D21H 17/21; D21H 17/22; D21H 17/24; D21H 21/16; C12P 19/04
USPC .......................................................... 162/175
See application file for complete search history.

(56) References Cited

U.S. PATENT DOCUMENTS 8,017,374 B2 *   9/2011   Kumar ..................... C02F 3/34
                                                         435/254.1

FOREIGN PATENT DOCUMENTS

| CN | 101864700 | 10/2010 | |
|---|---|---|---|
| DE | 23 54 713 | * 11/1973 | ............ C02F 212/08 |
| WO | 02/12623 | 2/2002 | |
| WO | 2015/057067 | 4/2015 | |

OTHER PUBLICATIONS

DE 23 54 713, Scharf et al., Nov. 1973, translation.*

* cited by examiner

*Primary Examiner* — Mark Halpern
(74) *Attorney, Agent, or Firm* — Peacock Law P.C.; Jeffrey D. Myers; Janeen Vilven

(57) ABSTRACT

An invention in the field of papermaking that relates in particular to sizing paper. Problems with state of the art methods are that the sizing chemicals used are typically expensive; may be available only in limited supply; are produced using methods that are damaging to the environment; and whose production is far from carbon-neutral. It is an object of the present invention to provide an alternative to the methods of the prior art and to overcome one or more of the above mentioned disadvantages.

1 Claim, 5 Drawing Sheets

EXTRACELLULAR POLYMERS FROM GRANULAR SLUDGE AS SIZING AGENTS

CROSS-REFERENCE TO RELATED APPLICATIONS

This application is a continuation of International Patent Application WO2015/057067 A1, filed Oct. 14, 2014, in the name of "Technische Universiteit Delft", which PCT-application claims priority to Netherlands Patent Application with Serial No. 2011609, filed Oct. 14, 2013, in the name of "Technische Universiteit Delft", and the specifications and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

Field of the Invention (Technical Field)
The present invention is in the field of papermaking and relates in particular to sizing paper.
Background of the Invention
In the papermaking field, it is known that most paper is made of cellulose and/or hemicellulose fibres. These fibres contain hydroxyl groups. Hydrogen bonding between water molecules and the hydroxyl groups of the cellulose and/or hemicellulose fibres is energetically favourable and thus water can readily wet and penetrate paper. In other words, paper is not water resistant.

A problem that this poses is that for paper to be useful in e.g. printing, writing, packaging, wrapping, and construction applications, it needs to have a degree of water resistance. To overcome this problem, paper is usually treated with sizing chemicals either during manufacture of the paper (internal sizing) or by surface treatment of the paper (surface sizing).

Sizing relates to a process for making paper at least partially water resistant by the addition of polymers. Typical examples of sizing chemicals include: carbohydrates, such as starches, gums, and alginates; amphipathic compounds, such as rosin, and alkyl ketene dimer; and, alkenyl succinic anhydride.

Methods for sizing paper are known from e.g. CN101864700A which recites a surface treatment method capable of improving surface smoothness of light paper and reducing printing ink absorbability. WO2002/012623 A recites a process for sizing paper which comprises adding to an aqueous suspension containing cellulosic fibres, and optional fillers, (i) an anionic or cationic sizing dispersion; and (ii) a sizing promoter comprising a cationic organic polymer having one or more aromatic groups, and an anionic polymer having one or more aromatic groups, the anionic polymer being a step-growth polymer, a polysaccharide or a naturally occurring aromatic polymer, forming and draining the obtained suspension, wherein the sizing dispersion and sizing promoter are added separately to the aqueous suspension.

Problems associated with such methods are e.g. that the sizing chemicals used are typically expensive; they may be available only in limited supply; they are produced using methods that are damaging to the environment; and whose production is far from carbon-neutral.

It is an object of the present invention to overcome one or more of the disadvantages of the prior art, without jeopardizing functionality and advantages.

BRIEF SUMMARY OF THE INVENTION

In a first aspect, the present invention relates to use of extracellular polymeric substances obtainable from granular sludge for sizing paper or any paper-like product.

At present, the sludge produced from wastewater treatment processes, including granular sludge, is considered as a waste product, having no further use. On top of that, costs of waste disposal are 500-600€ per ton of sludge in the Netherlands. This represents roughly one third of the wastewater treatment costs.

Surprisingly, it has been found that extracellular polymeric substances obtainable from granular sludge are suitable and effective for sizing paper. The present invention therefore provides a commercially and environmentally very interesting application of this 'waste' product.

Granules making up granular sludge are aggregates of microbial cells self-immobilized through extracellular polymeric substances into a spherical form without any involvement of carrier material. A characterising feature of granules of granular sludge is that they do not significantly coagulate during settling (i.e. in a reactor under reduced hydrodynamic shear).

Extracellular polymeric substances make up a significant proportion of the total mass of the granules.

Extracellular polymeric substances comprise high-molecular weight compounds (typically>5 kDa) secreted by microorganisms into their environment. Extracellular polymeric substances are mostly composed of polysaccharides and proteins, but include other macro-molecules such as DNA, lipids and humic substances.

Extracellular polymeric substances obtainable from granular sludge (preferably obtained from granular sludge) do not require further purification or treatment to be used for sizing paper. Wherein the extracellular polymeric substances are obtained from granular sludge the extracellular polymeric substances are preferably isolated from bacteria (cells) and/or other non-extracellular polymeric substances. An example of a suitable technique for isolating extracellular polymeric substances from granular sludge is given in the detailed description of the invention and accompanying example.

Advantageously, granules of granular sludge can be readily removed from a reactor by e.g. physical separation, settling, centrifugation, cyclonic separation, decantation, filtration, or sieving to provide extracellular polymeric substances in a small volume. Compared to separating material from a liquid phase of the reactor this means that neither huge volumes of organic nor other solvents (for extraction), nor large amounts of energy (to evaporate the liquid) are required for isolation of the extracellular polymeric substances.

Thereby the present invention provides a solution to one or more of the above mentioned problems.

Advantages of the present description are detailed throughout the description.

DETAILED DESCRIPTION OF THE INVENTION

The present invention relates to use of extracellular polymeric substances obtainable from granular sludge for sizing paper or any paper-like product.

In an example, the extracellular polymeric substances comprise a major portion consisting of exopolysaccharides, and a minor portion, such as less than 30% w/w, typically less than 10% w/w, consisting of lipids and/or other components more hydrophobic than the exopolysaccharides.

The weight percentages (w/w) throughout the description are based on a total weight of a (dry) composition.

Extracellular polymeric substances obtained from granular sludge having a major portion of exopolysaccharides and a minor portion of lipids have been found to provide very effective water resistance to paper, in particular when the extracellular polymeric substances are used for surface sizing, i.e. where the extracellular polymeric substances are at an air-interface of the paper.

In an example, the extracellular polymeric substances comprise at least 50% w/w exopolysaccharides, preferably at least 60% w/w exopolysaccharides, most preferably at least 75% w/w exopolysaccharides, such as at least 90% w/w exopolysaccharides. Extracellular polymeric substances obtained from granular sludge have been found to be particularly effective sizing agents when they have a high exopolysaccharide content. The exopolysaccharide content is preferably not 100%, as a remainder has been found to contribute to the present advantages effects.

In an example, the granular sludge is aerobic granular sludge or anammox granular sludge. Extracellular polymeric substances obtained from aerobic granular sludge and anammox granular sludge have been shown to be particularly effective as sizing agents. Research by the inventors has shown that exopolysaccharides of the extracellular polymeric substances obtained from aerobic granular sludge are alginate-like in character, and in fact perform even better than alginate per se as a sizing chemical. Sizing with alginate per se is known in the prior art.

Aerobic granular sludge and anammox granular sludge, and the processes used for obtaining them are known to a person skilled in the art. For the uninitiated, reference is made to *Water Research,* 2007, doi:10.1016/j.watres.2007.03.044 (anammox granular sludge) and *Water Science and Technology,* 2007, 55(8-9), 75-81 (aerobic granular sludge).

In an example, the extracellular polymeric substances have been obtained from aerobic or anammox granular sludge by an isolation (i.e. separation) method comprising: alkaline extraction of the granular sludge thereby forming extracellular polymeric substances containing extractant; acid precipitation of extracellular polymeric substances from the extractant; and collecting the extracellular polymeric substance-containing precipitate.

It has been found that this method is particularly effective for obtaining extracellular polymeric substances from granular sludge, such as from aerobic and anammox granular sludge, in good yield.

In an example, the granular sludge has been substantially produced by bacteria belonging to the order Pseudomonadaceae, such as *pseudomonas* and/or *Azotobacter* bacteria (aerobic granular sludge); or, by bacteria belonging to the order Planctomycetales (anammox granular sludge), such as *Brocadia anammoxidans, Kuenenia stuttgartiensis* or *Brocadia fulgida*; or, combinations thereof. Extracellular polymeric substances from granular sludge produced by these bacteria are effective sizing agents, even when applied in an amount in the range of 0.1-5% w/w extracellular polymeric substances/final product.

In an example, the exopolysaccharides are block-copolymers comprising uronic acid (e.g. mannuronic acid and guluronic acid) residues.

In an example, the extracellular polymeric substances are in aqueous solution at a concentration in the range of 0.1-30% w/w, preferably 1-10% w/w, most preferably 4-10% w/w, such as 5-8% w/w. Such provides a solution having suitable characteristics for spraying. Thereby a uniform layer of the extracellular polymeric substances can be provided on paper, (largely) after the paper has been produced.

In an example, the extracellular polymeric substances are added to the paper forming solution and/or to the paper, i.e. forming part of a paper production process.

In an example, the extracellular polymeric substances are bleached, such as by treatment with hydrogen peroxide. By bleaching the extracellular polymeric substances, they can be used for sizing white and coloured paper without changing the colour of the paper. Surprisingly, bleaching with e.g. hydrogen peroxide only slightly reduces the sizing performance of the extracellular polymeric substances (the amount applied is preferably increased by around 20-40% compared (relative) to unbleached extracellular polymeric substances).

In a second aspect, the present invention relates to a method for sizing paper comprising: (i) feeding a reactor with (a) waste water, such as obtained from manufacturing of paper thereby providing a carbon source, and (b) granular sludge forming bacteria; (ii) operating the reactor under suitable conditions for generating and growing granular sludge; (iii) separating at least a proportion of granules of the granular sludge, such as by physical separation, settling, centrifugation, cyclonic separation, decantation, filtration, or sieving; (iv) separating extracellular polymeric substances from the collected aerobic granular sludge; and (v) sizing paper with the extracellular polymeric substances.

In an example, the granular sludge forming bacteria belong to the order *Pseudomonas* and *Azotobacter*, and step (ii) above comprises: (ii) (a) in a first stage maintaining the reactor under low oxygen concentration conditions (anaerobic) during a predetermined period of time at a predetermined temperature for accumulating carbon in cells of the bacteria; and (ii) (b) in a second stage maintaining the reactor under high oxy-gen concentration conditions (aerobic) during a predetermined period of time at a predetermined temperature for growing the bacteria in granular form so as to form granules. The temperature is preferably in a range of 5-30° C., such as 10-25° C.

The oxygen concentration in the first stage is preferably as low as possible, e.g. with respect to a reactor set-up. The period of time in the first stage is in the order of 0.1-8 hours, preferably 0.25-4 hours, more preferably 0.5-2 hours, such as 1 hour.

The oxygen concentration in the second stage may be similar or equal to environmental conditions. It is noted that an oxygen concentration of 10% of a saturation value is considered high enough in this respect. In an example the second stage time is 3-48 hours, preferably 6-24 hours, more preferably 10-18 hours, such as 12 hours.

In an example, the granular sludge forming bacteria belong to the order Planctomycetales; wherein in step (i) the waste water further comprises an ammonium source; and wherein step (ii) comprises maintaining the reactor under high oxygen concentration conditions (aerobic).

In an example, the bacteria belonging to the order Pseudomonadaceae, such as *pseudomonas* and/or *Azotobacter*, preferably cultivated bacteria.

In a third aspect, the present invention relates to sized paper obtainable by a method according to the second aspect of the invention.

In a fourth aspect, the present invention relates to sized paper comprising extracellular polymeric substances from aerobic granular sludge and/or anammox granular sludge. In an amount of 0.1-5% w/w extracellular polymeric substances/final product.

The invention will hereafter be further elucidated with reference to the Example and Drawings which are exemplary and explanatory of nature and are not limiting the scope of the invention. To the person skilled in the art it may be clear that many variants and combinations thereof, being obvious or not, may be conceivable falling within the scope of protection, defined by the present claims.

EXAMPLE

Using Extracellular Polymeric Substances Obtain able (EPS) from aerobic granular sludge to increase water resistance of paper fibre.

DETAILED DESCRIPTION OF FIGURES

Figure 1:
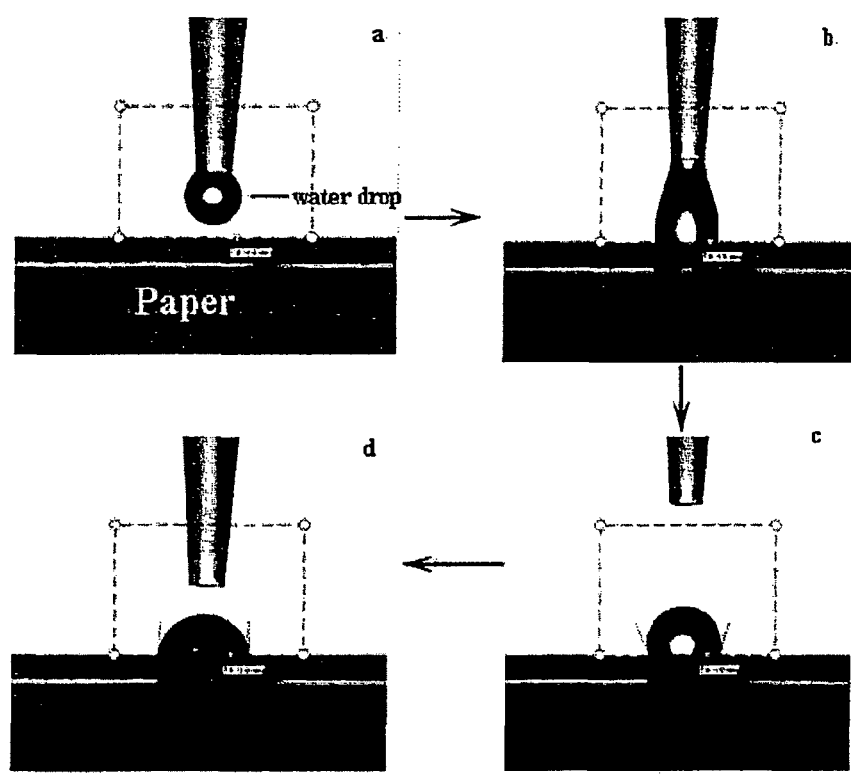
FIG. 1—Contact angle measurement. After the water drop fell on the paper (b), the contact angle (the angle at which the liquid-vapor interface meets the solid-liquid interface) of the water drop was monitored for 120 seconds (c→d).

The figures are further detailed in the description of the experiments below.

Examples/Experiments

Methods

Aerobic Granular Sludge for Investigation

The aerobic granular sludge from which the extracellular polymeric substances of the present example were obtained was collected from the Nereda® pilot plant, operated by DHV at the wastewater treatment plant Epe, The Netherlands. The reactor was fed with municipal sewage. The influent consisted of approximately 25% of slaughterhouse wastewater, which was discharged in the sewage system. Average parameters of the influent were: CODtotal 585 mg/L, suspended solids 195 mg/L, $NH_4$—N 55 mg/L and $PO_4$—P 6.3 mg/L. The reactor was operated in Sequencing Batch (SBR) mode for biological phosphate and nitrogen removal. Operational details were described in Lin et al. (2010). After start-up, biomass concentration in the reactor was maintained around 8 to 10 g TSS/L. Oxygen in the reactor was controlled between 2 to 3 mg/L during aeration. Temperature and pH were not controlled in this system and depended on the incoming sewage. During steady operation, aerobic granular sludge was collected and sieved to give granules with a diameter>2 mm.

The granules were then dried.

Isolation of Extracellular Polymeric Substances

Dried granules (0.5 g) were homogenized for 5 min (Labgen tissue homogenizer, Cole-Parmer, USA) and extracted in 80 ml 0.2M $Na_2CO_3$ at 80° C. for 1 h. After centrifuging at 15,000 rpm for 20 min, the pellet was discarded. The supernatant pH was adjusted to 2 by adding 0.1 M HCl. The precipitate was collected by centrifugation (15,000 rpm, 30 min), washed by dideionized water until effluent pH reached 7, and dissolved in 0.1 M NaOH. Extracellular polymeric substances in the supernatant were precipitated by the addition of cold absolute ethanol to a final concentration of 80% (vol/vol). The precipitate was collected by centrifugation (15,000 rpm, 30 min), washed three times in absolute ethanol and lyophilized. The resulting mixture of extracellular polymer substances is an example of extracellular polymeric substances (EPS) obtainable from granular sludge according to the invention.

Ash content of the EPS was measured according to the standard method (APHA).

Characterisation of EPS

Before characterisation, EPS (0.5 g) was dissolved in 15 mL of NaOH solution (0.05M). The pH was then adjusted to 7.0 by 0.05 M HCl. Finally the solution was placed inside a dialysis tubing (3500 MWCO) and dialyzed against demineralized water for 48 hours to remove loosely bound ions and lyophilized.

Morphology of EPS by Atomic Force Microscopy

Imaging of EPS was carried out in air at ambient temperature and humidity using freshly-cleaved mica pretreated by 3 mM $NiCl_3$. Aliquots (2 ul) of extracellular polymeric substances (5 mg/L) were deposited onto mica surfaces for 10 s, and then quickly removed by the pipette. Those surfaces were air dried (1 h) in a dust-free enclosure. Samples were scanned with a Digital Instruments Multi-mode atomic force microscope (Veeco nanoscopy iva dimension 3100, Veeco Inc., Santa Barbara, USA).

EPS Composition Analysis by Pyrolysis-Gas Chromatography-Mass Spectrometry

Pyrolysis was carried out on a Horizon Instruments Curie-Point pyrolyser. The lyophilized extracellular polymeric substances were heated for 5 s at 600° C. The pyrolysis unit was connected to a Carlo Erba GC8060 gas chromatograph and the products were separated by a fused silica column (Varian, 25 m, 0.25 mm i.d.) coated with CP-Sil5 (film thickness 0.40 μm). Helium was used as carrier gas. The oven was initially kept at 40° C. for 1 min, next it was heated at a rate of 7° C./min to 320° C. and maintained at that temperature for 15 min. The column was coupled to a Fisons MD800 mass spectrometer (mass range m/z 45-650, ionization energy 70 eV, cycle time 0.7 s). Identification of the compounds was carried out by their mass spectra using a NIST library or by interpretation of the spectra, by their retention times and/or by comparison with literature data.

Lipid Content of EPS

For lipids analysis in the extracellular polymeric substances, the methods proposed by Smolders et al. (1994) were used with modification. Pure fatty acids (Sigma-Aldrich) were used as external standard. Freeze-dried extracellular polymeric substance samples and fatty acid standards were weighed using an analytical balance and transferred into tubes with screw caps. One milligramme of C15 fatty acid in 1-propanol was used as internal standard. 1.5 mL of a mixture of concentrated HCl and 1-propanol (1:4), and 1.5 mL of dichloroethane were added into the tubes and heated for 2 h at 100° C. After cooling, free acids were extracted from the organic phase with 3 mL water. One milliliter of the organic phase was filtered over water-free sodium sulphate into GC vials. The lipids in the organic phase were analyzed by gas chromatography (model 6890N, Agilent, USA) equipped with a FID, on an HP Innowax column.

EPS Molecular Weight Analysis

Size exclusion chromatography was performed with a Superdex 75 10/300 GL column (AKTA Purifier System, GE Healthcare). Elution was carried out at room temperature using PBS at constant 0.4 mL/min flow rate and detection was monitored by following the absorbance of the eluted molecules at 210 nm. Superdex 75 10/300 GL (GE Healthcare) column separates molecules of 1 000 to 150 000 Daltons (Da) with a total exclusion volume of 7.9 mL. Measurement of the elution volume of dextran standards (1000 Da, 5000 Da, 12000 Da, 25 000 Da and 50 000 Da) led to the calibration equation:

$$Log(MW)=6.212-0.1861 Ve$$

MW: Molecular Weight of the molecule in Dalton (Da)
Ve: elution volume in mL (assayed at the top of the peak)

Chromatogram profiles were recorded with UNICORN 5.1 software (GE Healthcare). Peak retention times and peak areas were directly calculated and delivered by the program.

Bleaching of EPS

EPS (1 g) was put into $H_2O_2$ (30%) for 24 hours, collected by centrifuge at 4000 rpm and lyophilized.

Sizing with EPS and Water Resistance Property of Paper after Sizing with EPS 1 mL of both the unbleached (5% w/w) and bleached EPS (8% w/w) were sprayed evenly on pieces of raw paper (10 cm×10 cm, 96 g/m2, without the addition of any sizing chemicals, supplied by Kenniscentrum Papier en Karton, the Netherlands), and air-dried. 1 ml of one commercial sizing chemical (Impermax WRP 50C, supplied by Kenniscentrum Papier en Karton), was sprayed on the same kind of paper with the same size and air-dried. The change of contact angle (the contact angle is the angle at which the liquid-vapor interface meets the solid-liquid interface) with time of a drop of miliQ water on these air-dried pieces of paper was recorded and measured by KSV CAM200 (FIG. 1).

The change of contact angle with time of a drop of miliQ water on the raw paper itself was also recorded and measured as a control.

On each piece of paper, the contact angle was measured at 5 different places randomly; the average value and standard deviation were calculated.

Results

Extracellular polymeric substances were obtained from aerobic granular sludge as described above. The extracellular polymeric substances were then characterised and used in sizing paper. The sized layer was finally tested for its effectiveness.

Morphology of Extracellular Polymeric Substances by the Atomic Force Microscope

Figure 2:
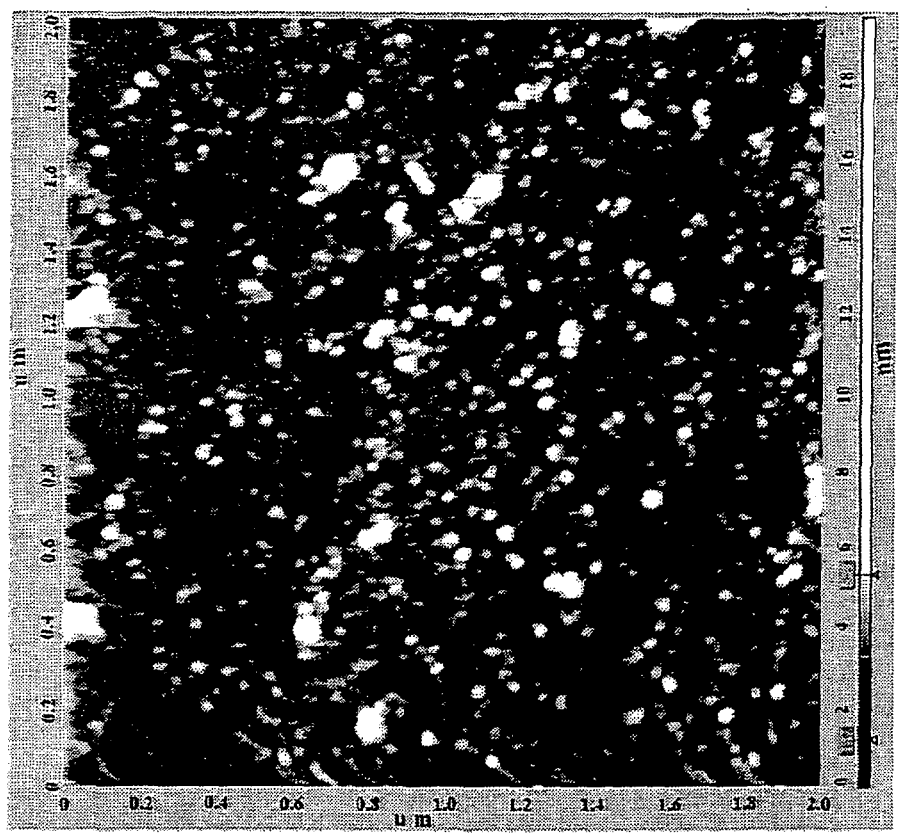
FIG. 2—Morphology of extracellular polymeric substances from aerobic granular sludge by atomic force microscopy. The fibre-like structure covers the surface and forms film; the globules distribute on the film and point to the air.

See FIG. 2.

The yield of extracellular polymeric substances was 160±4 mg/g (VSS ratio).

The extracellular polymeric substances have a fibre-like structure. The width of the fibre is around 20 nm (FIG. 2). The fibres extend along the surface and entangle with each other, forming a web-like structure that covers the whole surface of the mica. This demonstrates that the extracellular polymeric substances have a perfect film-forming property and can form a continuous film on a surface. The thickness of extracellular polymeric substance film is around 4 nm. In addition to the fibres, there are a few globules distributing on the fibres and pointing to the air. The height of the globules can reach 15 nm, which is 2 times higher than the thickness of extracellular polymeric substance film. Due to the significant difference in height, the globules looked much brighter than the fibres under the atomic force microscope. As the sample was prepared by depositing extracellular polymeric substance water solution on a surface and air dried, those globules extending out of the surface and pointing to the air must have hydrophobic property.

Figure 3:
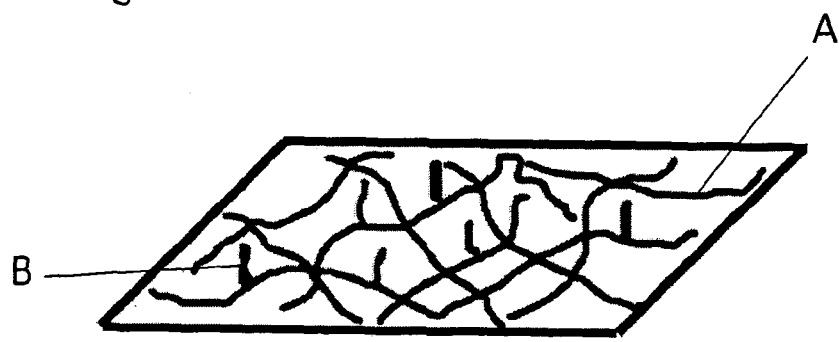
FIG. 3—Diagram of extracellular polymeric substances at the surface between water and air. The hydrophilic parts cover the surface and hydrophobic parts point to the air.

Therefore, the extracellular polymeric substances have both a hydrophilic part and hydrophobic part. When the extracellular polymeric substances stay at the surface between water and air, the hydrophilic parts spread along the surface, forming a film and the hydrophobic parts distribute on the film and pointing to the air (FIG. 3).

Extracellular Polymeric Substance Composition Analysis

Figure 4:
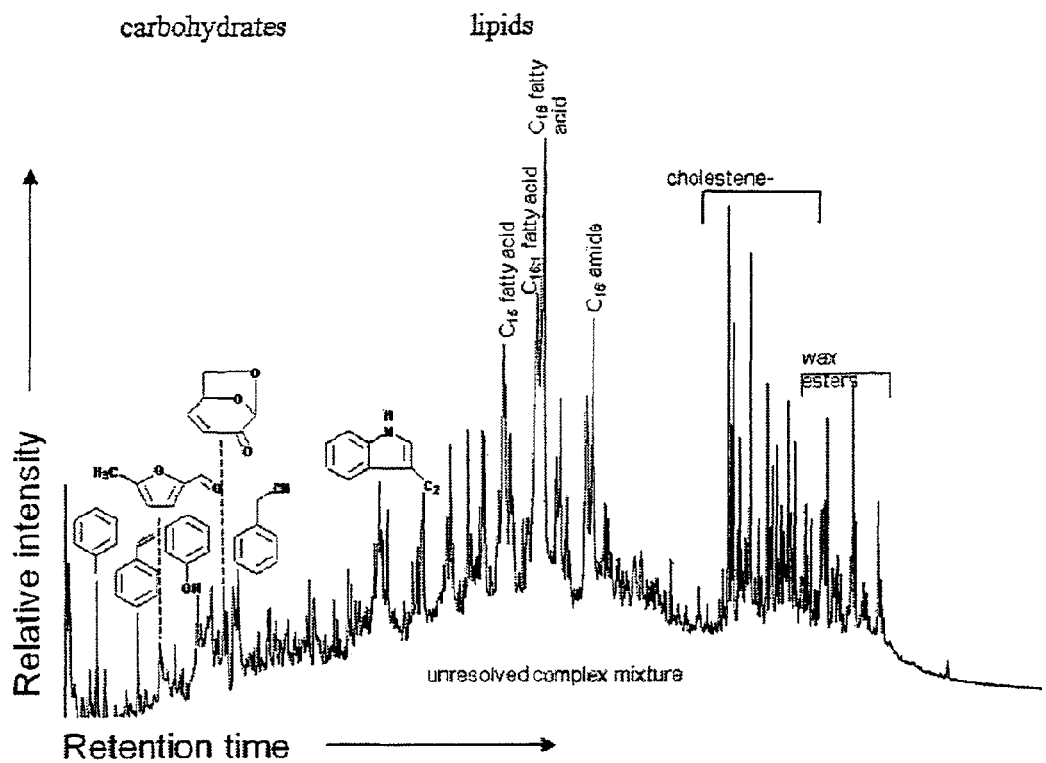
FIG. 4—Pyrolysis-gas chromatograms of extracellular polymeric substances from aerobic granular sludge. Cn and Cn:1 indicates chain length of saturated and unsaturated compounds.

The composition of the extracellular polymeric substances was analysed by pyrolysis-GC-MS. In the spectrum (FIG. 4), polysaccharide-derived products such as 5-methylfuraldhyde and levoglucosenone were identified, implying a contribution from carbohydrate units to the extracellular polymeric substance sample. Lipids and wax esters composed of C16 and C18 fatty acids and alcohol moieties of the same carbon lengths were found as well. By contrast, all pyrolysis products of proteins and other combinations of amino acids were much less prominent, indicating that they were relatively minor components of the extracellular polymeric substances. In addition, there is a so-called unresolved complex mixture consisting of many similar compounds that co-elute and which cannot be identified by their mass spectra at present. In brief, the pyrolysis-GC-MS analysis displays that, comparing to carbohydrates and lipids, proteins are a minor part of the extracellular polymeric substances.

The lipid content in the extracellular polymeric substances was measured as 8.2±0.9 mg/g extracellular polymeric substances.

Since normally polysaccharides are hydrophilic and lipids are hydrophobic, comparing to the morphology in FIG. 2, it can be assumed that the fibre-like structure which forms film on the surface are mostly polysaccharides and those globules pointing towards the air are mostly lipids.

Molecular Weight of Extracellular Polymeric Substances

Figure 5:
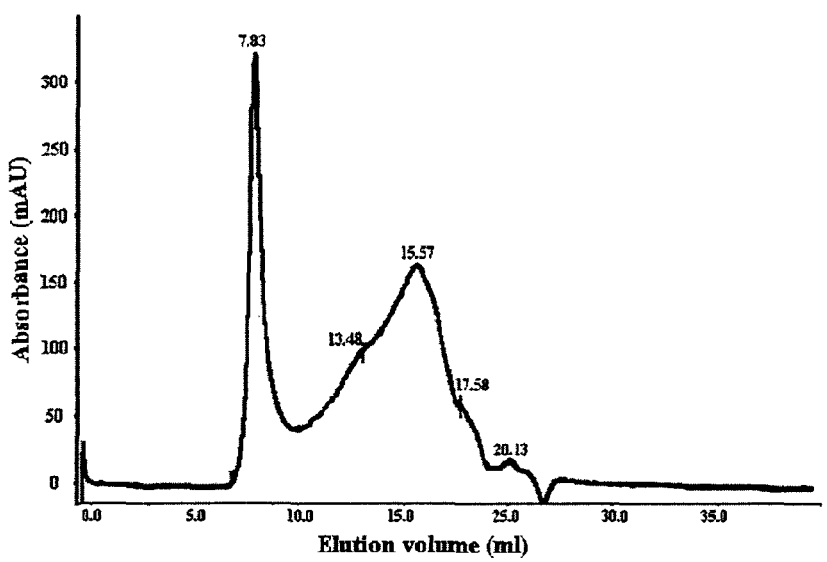
FIG. 5—Size distribution profiles of extracellular polymeric substances from aerobic granular sludge by size exclusion chromatography.

The size distribution profile of the extracellular polymeric substances by size exclusion chromatography is shown in FIG. 5. There are 5 fractions with different elution volume. The fraction with the shortest elution volume, which has the highest molecular weight, separate well with other fractions. The three fractions with an elution volume between 13 ml to 17 ml co-eluted. The molecular weight of these 5 fractions and their percentages are listed in Table 1. It can be clearly seen that most of isolated extracellular polymeric substances (94%) has a molecular weight of more than 5.8 KDa, and about ⅓ of the extracellular polymeric substances has a molecular weight higher than 150 KDa. As carbohydrates with higher molecular weight tend to extend on the surface, it could be an explanation for the perfect film-forming property of the isolated extracellular polymeric substances.

TABLE 1

Molecular weight of different fractions in extracellular polymeric substances isolated from granular sludge and their percentage.

| Elution volume of the peak (ml) | Molecular weight (Da) | Percentage of the fraction (% peak area) |
|---|---|---|
| 7.83 | $7 \times 10^4$ | 29.74 |
| 13.48 | $1.44 \times 10^4$ | 18.82 |
| 15.57 | $5.79 \times 10^3$ | 45.15 |
| 17.58 | $2.15 \times 10^3$ | 4.42 |
| 20.13 | $6.56 \times 10^2$ | 1.87 |

Use of Extracellular Polymeric Substances as a Sizing Chemical in Papermaking

Figure 6:
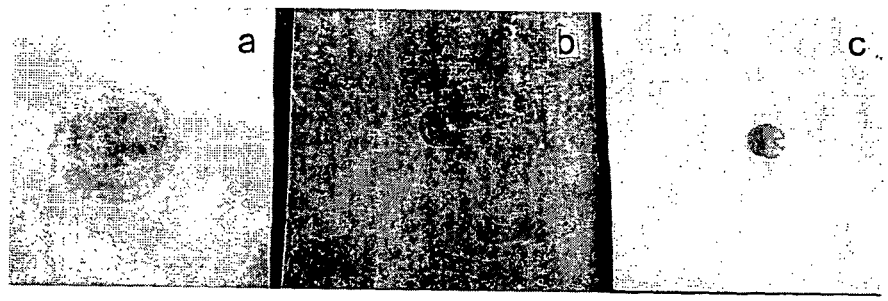
FIG. 6—Water drops on paper (a): raw paper; (b): paper coated with 5% extracellular polymeric substances; (c): paper coated with 8% bleached extracellular polymeric substances.

The effect of bleached and unbleached extracellular polymeric substances on increasing the water resistance of paper is shown in FIG. 6. For unsized paper, once a drop of water falls on the surface, it is absorbed immediately by the paper and rapidly spreads. In contrast, the water retains the shape of the drop on extracellular polymeric substances and bleached extracellular polymeric substances coated paper sheets.

Figure 7:
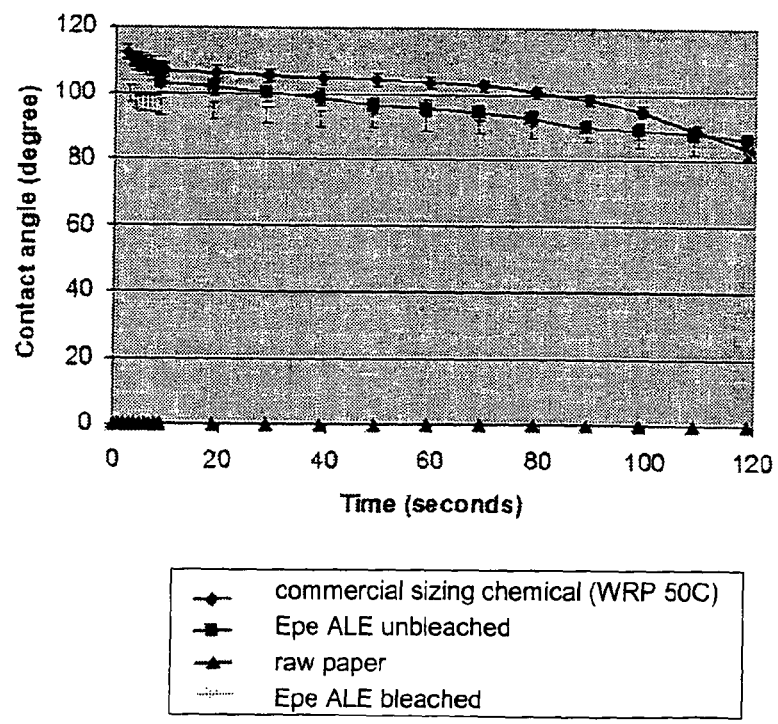
FIG. 7—The contact angle of miliQ water on the raw paper, paper coated with the commercial sizing chemical WRP 50C and with bleached and unbleached extracellular polymeric substances as a function of time.

To evaluate the water resistance property, the contact angle between the water droplet and the surface of the paper was monitored within 120 seconds (FIG. 7). Water in contact with the unsized paper is absorbed in less than 1 s. But for paper sheets sized with a 5% extracellular substances solution and 8% bleached extracellular polymeric substances solution, their water resistance property is comparable to paper sheet sized with a commercial sizing product (10% of alkenyl succinic anhydride). Both of their initial contact angles are higher than 100, which fulfil the requirement of an adequately sized paper. The extracellular polymeric substances as obtained from granular sludge have a brown colour, bleaching with $H_2O_2$ results in a colourless substance.

It is thought that the good sizing performance of extracellular polymeric substances obtainable from granular sludge is at least in part due to it comprising both hydrophilic and hydrophobic components. Such also distinguishes it from sizing agents presently used.

Figure 8:
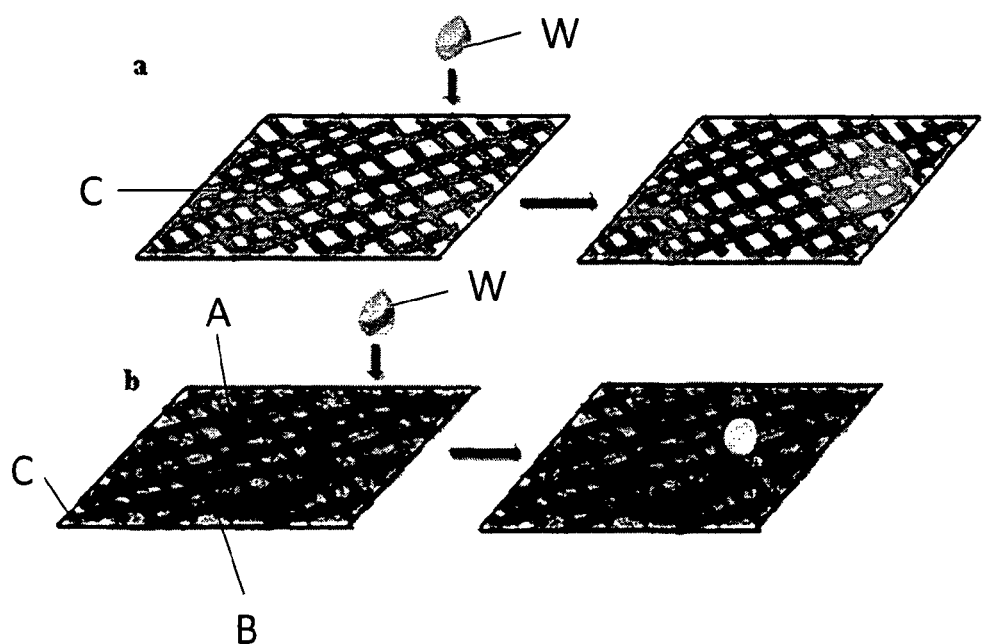
FIG. 8—Diagram of the water resistance effect of extracellular polymeric substances on cellulosic fibre. a: cellulosic fibres are porous (there are empty voids between the fibres), water is easily wet and penetrate the fibre network. b: The extracellular polymeric substances are fibre-like material, but these fibres are 20 nm in width, which is at least 1000 times thinner than cellulosic fibre. Extracellular polymeric substance forms a film on cellulose fibre. Due to the existence of the hydrophobic part of extracellular polymeric substance, the water drop does not easily wet and run through the fibre.

This is explained with reference to FIG. 8.

The width of the cellulosic fibre in paper is around 20 μm; when a cellulose fibre network is formed, significant amount of empty voids present between the fibres. However, the width of the fibre of the extracellular polymeric substance is on average, only 20 nm. Thus, it is thought that these nanofibres can entangle with each other and form a web-like film which covers both the surface of the cellulosic fibres and the empty voids. At the same time, the hydrophobic globules extend to the air. When a water drop comes into contact with the surface of the paper sheet sized with extracellular polymeric substances, the repulsion force from the hydrophobic globules will keep the water as a drop. Even with water in contact with the hydrophilic fibres of the extracellular polymeric substance, it will be absorbed only slowly by extracellular polymeric substances due to swelling without wetting the cellulosic fibre and spreading.

Extracellular polymeric substances from granular sludge provide an effective and green alternative to current commercial sizing agents.

The invention although described in detailed explanatory context may be best understood in conjunction with the accompanying examples and figures.

It should be appreciated that for commercial application it may be preferable to use one or more variations of the present system, which would similar be to the ones disclosed in the present application and are within the spirit of the invention.

What is claimed is:

1. Sized paper comprising extracellular polymeric substances obtainable from aerobic granular sludge and/or anammox granular sludge.

* * * * *